United States Patent [19]
Zetlmeisl

[11] Patent Number: 5,863,415
[45] Date of Patent: *Jan. 26, 1999

[54] CONTROL OF NAPHTHENIC ACID CORROSION WITH THIOPHOSPORUS COMPOUNDS

[75] Inventor: Michael J. Zetlmeisl, St. Louis, Mo.

[73] Assignee: Baker Hughes Incorporated, Houston, Tex.

[*] Notice: This patent issued on a continued prosecution application filed under 37 CFR 1.53(d), and is subject to the twenty year patent term provisions of 35 U.S.C. 154(a)(2).

[21] Appl. No.: 919,839

[22] Filed: Aug. 28, 1997

Related U.S. Application Data

[63] Continuation of Ser. No. 655,615, May 30, 1996.

[51] Int. Cl.[6] .......................... C23F 11/167; C23F 11/12; C23F 11/16
[52] U.S. Cl. .................. 208/47; 252/389.2; 252/389.22; 422/15; 507/128; 507/235
[58] Field of Search .................. 252/389.21, 389.23, 252/389.22; 208/48 AA, 47; 507/128, 235; 422/15

[56] References Cited

U.S. PATENT DOCUMENTS

| | | | |
|---|---|---|---|
| 3,668,111 | 6/1972 | Dvoracek et al. | 208/48 AA |
| 3,856,687 | 12/1974 | Lowe | 252/33.4 |
| 3,909,447 | 9/1975 | Alink et al. | 548/111 |
| 4,024,051 | 5/1977 | Shell et al. | 208/348 |
| 4,075,291 | 2/1978 | Redmore et al. | 260/933 |
| 4,491,994 | 1/1985 | Zetlmeisl et al. | 252/389.23 |
| 4,578,178 | 3/1986 | Forester | 208/48 AA |
| 4,775,458 | 10/1988 | Forester | 208/48 AA |
| 4,775,459 | 10/1988 | Forester | 208/48 AA |
| 4,804,456 | 2/1989 | Forester | 208/48 AA |
| 5,182,013 | 1/1993 | Petersen et al. | 208/348 |
| 5,252,254 | 10/1993 | Babaian-Kibala | 252/393 |
| 5,314,643 | 5/1994 | Edmondson et al. | 252/389.23 |
| 5,472,637 | 12/1995 | Hart | 252/358 |
| 5,552,085 | 9/1996 | Babaian-Kibala | 252/389.23 |

OTHER PUBLICATIONS

Zetlmeisl, Michael J. "A Laboratory and Field Investigation of Naphthenic Acid Corrosion Inhibition", Corrosion 95, Paper No. 334.

Babaian–Kibala, Elizabeth, et al., "Naphthenic Acid Corrosion in a Refinery Setting", Corrosion 93, Paper No. 631.

Lubrizol Performance Products Company, Product Data Sheet for Lubrizol® 2602.

Lubrizol Performance Products Company, Product Data Sheet for Lubrizol® 5950.

*Primary Examiner*—Benjamin Utech
*Assistant Examiner*—Deanna Baxam
*Attorney, Agent, or Firm*—Howell & Haferkamp, L.C.

[57] ABSTRACT

Corrosion of iron-containing metal surfaces in a hydrocarbon fluid having a temperature of from about 175° C. to about 400° C. and containing a corrosive amount of naphthenic acid is inhibited by adding to the fluid or to a feed therefor, in a total additive amount sufficient to effect corrosion inhibition in said fluid, one or more thiophosphorus compound, a salt thereof, an alkyl or aryl ester thereof, an isomer thereof, or some combination of the foregoing, thereby to effect inhibition of naphthenic acid induced corrosion in the fluid.

37 Claims, No Drawings

CONTROL OF NAPHTHENIC ACID CORROSION WITH THIOPHOSPORUS COMPOUNDS

This application is a continuation of copending application Ser. No. 08/655,615 filed on May 30, 1996.

BACKGROUND OF THE INVENTION

(1) Field of the Invention

The present invention relates to the inhibition of metal corrosion in acidic hot hydrocarbons, and more particularly to the inhibition of corrosion of iron-containing metals in hot acidic hydrocarbons, especially when the acidity is derived from the presence of naphthenic acid.

(2) Description of the Prior Art

It is widely known in the art that the processing of crude oil in its various fractions has led to damage of the iron-containing metal surfaces of associated apparatus due to naphthenic acid corrosion. Generally speaking, naphthenic acid corrosion occurs when the crude being processed has a neutralization number or total acid number (TAN), expressed as the milligrams of potassium hydroxide required to neutralize the acids in a one gram sample, greater than 0.5. The corrosive problem is known to be aggravated by the elevated temperatures necessary to refine and crack the oil and by the oil's acidity which is caused primarily by high levels of naphthenic acid indigenous to the crudes. Sulfur in the crudes, which produces hydrogen sulfide at higher temperatures, also aggravates the problem. The temperature range of primary interest for this type of corrosion is in the range of about 175° C. to about 400° C., especially about 205° C. to about 400° C.

While various corrosion inhibitors are known in various arts, the efficacy and usefulness of any particular corrosion inhibitor is dependent on the particular circumstances in which it is applied. Thus, efficacy or usefulness under one set of circumstances often does not imply the same for another set of circumstances. As a result, a large number of corrosion inhibitors have been developed and are in use for application to various systems depending on the medium treated, the type of surface that is susceptible to the corrosion, the type of corrosion encountered, and the conditions to which the medium is exposed. For example, U.S. Pat. No. 3,909,447 describes certain corrosion inhibitors as useful against corrosion in relatively low temperature oxygenated aqueous systems such as water floods, cooling towers, drilling muds, air drilling and auto radiator systems. That patent also notes that many corrosion inhibitors capable of performing in non-aqueous systems and/or non-oxygenated systems perform poorly in aqueous and/or oxygenated systems. The reverse is true as well. The mere fact that an inhibitor that has shown efficacy in oxygenated aqueous systems does not suggest that it would show efficacy in a hydrocarbon. Moreover, the mere fact that an inhibitor has been efficacious at relatively low temperatures does not indicate that it would be efficacious at elevated temperatures. In fact, it is common for inhibitors that are very effective at relatively low temperatures to become ineffective at temperatures such as the 175° C. to 400° C. encountered in oil refining. At such temperatures, corrosion is notoriously troublesome and difficult to alleviate. Thus, U.S. Pat. No. 3,909,447 contains no teaching or suggestion that it would be effective in non-aqueous systems such as hydrocarbon fluids, especially hot hydrocarbon fluids. Nor is there any indication in U.S. Pat. No. 3,909,447 that the compounds disclosed therein would be effective against naphthenic acid corrosion under such conditions.

As commonly used, naphthenic acid is a collective term for certain organic acids present in various crude oils. Although there may be present minor amounts of other organic acids, it is understood that the majority of the acids in a naphthenic based crude are naphthenic in character, i.e., with a saturated ring structure as follows:

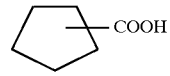

The molecular weight of naphthenic acid can extend over a large range. However, the majority of the naphthenic acid from crude oils is found in gas oil and light lubricating oil. When hydrocarbons containing such naphthenic acid contact iron-containing metals, especially at elevated temperatures, severe corrosion problems arise.

Various approaches to controlling naphthenic acid corrosion have included neutralization and/or removal of naphthenic acids from the crude being processed; blending low acid number oils with corrosive high acid number oils to reduce the overall neutralization number; and the use of relatively expensive corrosion-resistant alloys in the construction of apparatus used in the processing of crude oil. These attempts are generally disadvantageous in that they require additional processing and/or add substantial cost to treatment of the crude oil. Alternatively, U.S. Pat. No. 4,443,609 discloses certain tetrahydrothiazole phosphonic acids and esters as being useful as acid corrosion inhibitors. Such inhibitors can be prepared by reacting certain 2,5-dihydrothiazoles with a dialkyl phosphite. While these tetrahydrothiazole phosphonic acids or esters have good corrosion and inhibition properties, they tend to break down during high temperature applications thereof with possible emission of obnoxious and toxic substances.

It is also known that phosphorus-containing compounds impair the function of various catalysts used to treat crude oil, e.g., in fixed-bed hydrotreaters and hydrocracking units. Crude oil processors are often in a quandary since if the phosphite stabilizer is not used, then iron can accumulate in the hydrocarbon up to 10 to 20 ppm and impair the catalyst. Although nonphosphorus-containing inhibitors are commercially available, they are generally less effective than the phosphorus-containing compounds.

A significant advancement in phosphorus-containing naphthenic acid corrosion inhibitors was reported in U.S. Pat. No. 4,941,994, in which the present inventor is identified as a co-inventor. Therein it is disclosed that metal corrosion in hot acidic liquid hydrocarbons is inhibited by the presence of a corrosion inhibiting amount of a dialkyl and/or trialkyl phosphite with an optional thiazoline.

While the method described in U.S. Pat. No. 4,941,994 provides significant improvements over the prior art techniques, nevertheless, there is always a desire to enhance the ability of corrosion inhibitors while reducing the amount of phosphorus-containing compounds which may impair the function of various catalysts used to treat crude oil, as well as a desire for such inhibitors that may be produced from lower cost or more available starting materials.

SUMMARY OF THE INVENTION

Briefly, therefore, the present invention is directed to a novel method for inhibiting corrosion of iron-containing metal surfaces in a hydrocarbon fluid having a temperature of from about 175° C. to about 400° C. and containing a corrosive amount of naphthenic acid, wherein the method comprises adding to the fluid or to a feed therefor, in a total additive amount sufficient to effect corrosion inhibition in the fluid, at least one of the following types of compounds:

a. thiophosphorus compounds of the formula

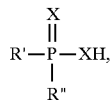

wherein R' is $R^3(OCH_2CH_2)_n$- or $R^3(OCH_2CH_2)_nO$—, R" is the same as R' or is —XH, each X is independently sulfur or oxygen, provided however that at least one X is sulfur, $R^3$ is an alkyl group of about 6 to about 18 carbon atoms and n is an integer from 0 to about 12, b. salts of such thiophosphorus compounds,
c. alkyl and aryl esters of such thiophosphorus compounds, and
d. isomers of such thiophosphorus compounds, such that the addition effects inhibition of naphthenic acid induced corrosion in the fluid.

Among the several advantages found to be achieved by the present invention, therefore, may be noted the provision of a method for inhibiting naphthenic acid corrosion with an inhibitor that remains stable at high temperatures; the provision of such method that provides improved corrosion inhibitive efficacy in high temperature hydrocarbon fluids; the provision of such method that uses less phosphorus than do conventional methods that employ phosphorus-based inhibitors; and the provision of such method that employs a naphthenic acid corrosion inhibitor which that may be prepared from relatively low cost starting materials.

DESCRIPTION OF THE PREFERRED EMBODIMENTS

In accordance with the present invention, it has been discovered that incorporating certain thiophosphorus compounds into a hydrocarbon fluid provides surprisingly effective inhibition of corrosion otherwise induced by the presence in the fluid of naphthenic acid, even though the fluid may be extremely hot, such as about 175° C. or even higher, yet may be prepared and used at a concentration that adds to the fluid less catalyst-impairing phosphorus than certain previous phosphorus-containing corrosion inhibitors. Moreover, the thiophosphorus compounds of the present invention may be prepared from relatively low cost starting materials.

Thus, the present invention is directed to naphthenic acid corrosion inhibition in hot hydrocarbon fluids. Of particular interest is corrosion inhibition in hydrocarbon fluids that are formed during crude oil refining processes; especially, gas oils and sometimes light lubricating oils. Such hydrocarbon fluids are typically heated to a temperature in the range of from about 175° C. to about 400° C., usually about 205° C. to about 400° C., at which temperatures the naphthenic acid corrosivity is extremely aggressive and difficult to inhibit.

Generally, corrosion inhibition in such hot hydrocarbon fluids may be afforded according to the present invention by adding to the hot hydrocarbon fluid, or to a feed to the fluid at least one of a few certain types of compounds. The feed may be a stream that is merely heated to become the hot hydrocarbon fluid or a stream that is somehow treated or otherwise converted into the hot hydrocarbon fluid, such as the feed to a distillation unit or a reactor. The additive or additives may be selected from among:

a. thiophosphorus compounds of the formula

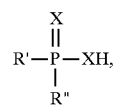

wherein R' is $R^3(OCH_2CH_2)_n$-, or $R^3(OCH_2CH_2)_nO$—, R" is the same as R' or is —XH, each X is independently sulfur or oxygen, provided however that at least one X is sulfur, $R^3$ is an alkyl group of about 6 to about 18 carbon atoms and n is an integer from 0 to about 12, b. salts of such thiophosphorus compounds,
c. alkyl and aryl esters of such thiophosphorus compounds, and
d. isomers of such thiophosphorus compounds.

Corrosion inhibition may be provided by the addition of just one composition of any of the mentioned types, or by some combination of compositions of one or more of such types. For example, a dose of a single alkyl dithiophosphoric acid of the formula

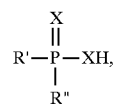

wherein R' and R" are each $R^3(OCH_2CH_2)_nO$—, each X is sulfur, $R^3$ is an alkyl group of about 8 to about 10 carbon atoms and n is an integer from about 3 to about 5, may be added to the fluid or feed therefor. Alternatively, two different compounds of the same type may be added in which, for instance, R' corresponds to $R^3(OCH_2CH_2)_nO$— for one of the compounds and corresponds to $R^3(OCH_2CH_2)_n$- for the other compound. And also alternatively, a thiophosphorus compound may be added along with an isomer thereof The combination of additives may be added to the fluid or feed in separate doses or they may be combined into an additive mixture and the mixture added to the fluid or feed.

As noted, one type of additive composition corresponds to thiophosphorus compounds of the formula

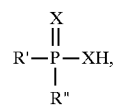

wherein R' is $R^3(OCH_2CH_2)_n$— or $R^3(OCH_2CH_2)_nO$—, R" is the same as R' or is —XH, each X is independently sulfur or oxygen, provided however that at least one X is sulfur, $R^3$ is an alkyl group of about 6 to about 18 carbon atoms and n is an integer from 0 to about 12. Preferably, R' and R" each corresponds to $R^3(OCH_2CH_2)_nO$— (most desirably R' and R" are the same) and each X is sulfur. It will be seen, therefore, that a preferred embodiment of the inhibitor is an alkyl dithiophophoric acid as described in U.S. Pat. No. 3,909,447, incorporated herein by reference. Compositions of that patent have been found to be effective in the hot hydrocarbon fluids of this invention, and the full scope of compositions described as within the scope of compositions in that patent are believed to be suitable here as well. Such compositions typically also comprise isomers of the thiophosphorus compounds as well, and such isomers will be discussed below.

Alkyl dithiophosporic acids within the scope of this invention, therefore, may correspond to the formula

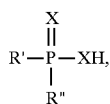

wherein each of R' and R" is $R^3(OCH_2CH_2)_nO-$ (R' usually being the same as R"), each X is sulfur, $R^3$ is an alkyl group of about 6 to about 18 carbon atoms and n is an integer from 0 to about 12. Preferably, $R^3$ is an alkyl from about eight to about ten, particularly where the compound has been prepared from Alfol 8-10, and n is from about 3 to about 5. However, the compound need not be ethoxylated and if not, n is 0. Preparation of alkyl dithiophosphoric acids are discussed in U. S. Pat. No. 3,909,447. Some are also commercially available.

Alternatively or additionally, the thiophosphorus compound may be a thiophosphinic acid. The thiophosphinic acid may correspond to the formula

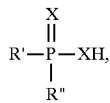

wherein each of R' and R" is $R^3(OCH_2CH_2)_n-$ (R' usually being the same as R"), one X (most preferably the X double bonded to the phosphorus) is sulfur and the other X is sulfur or oxygen (most preferably, sulfur), $R^3$ is an alkyl group of about 6 to about 18 carbon atoms and n is an integer from 0 to about 12. Preferred identities and ranges of the variables are as discussed with respect to the alkyl dithiophosphoric acids. Thiophosphinic acids are known and certain forms are commercially available.

Yet another form of the thiophosphorus compounds is a thiophosphonic acid, wherein the compound corresponds to the formula

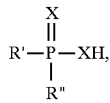

wherein R' is $R^3(OCH_2CH_2)_n-$, R" is —XH, one X (most preferably the X double bonded to the phosphorus) is sulfur and each of the other X's is sulfur or oxygen (most preferably, sulfur), $R^3$ is an alkyl group of about 6 to about 18 carbon atoms and n is an integer from 0 to about 12. Again, preferred identities and ranges of the variables are as discussed with respect to the alkyl dithiophosphoric acids.

The salts and alkyl and aryl esters of any of such thiophosphorus compounds may also be employed either in combination with the acids or in place of them. Exemplary types of suitable salts are discussed in U.S. Pat. No. 3,909, 447. Although they are discussed therein solely with respect to the alkyl dithiophosphoric acid, equivalent salts may be formed with the other thiophosphorus compounds. The esters may be formed by reaction of any of the noted thiophosphorus compounds with an alcohol. Preferred alcohols have up to about eighteen, preferably up to about twelve more carbon atoms. Thus, they are of the form R*OH wherein R* is an alkyl or aryl group of up to about eighteen, preferably up to about twelve, carbon atoms. Thus, the resulting ester has up to about eighteen, preferably up to about twelve, more carbon atoms than does the thiophosporus compound from which it is derived.

The isomers of the thiophosphorus compounds are generally dimers. Often, as discussed in U.S. Pat. No. 3,909,447, they are formed inherently in the preparation of the thiophosphorus compounds. In a preferred embodiment, therefore, the corrosion inhibitor additive is a mixture of alkyl dithiophosphoric acid and isomers thereof in accordance with the teachings of U.S. Pat. No. 3,909,447. However, as noted, the additive of this invention need not be such a mixture, but may be any of the discussed compounds individually or any combination of such compounds.

Generally, the isomers are of the formula

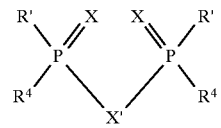

wherein X represents sulfur, X' represents sulfur or oxygen, R' is as defined above and $R^4$ is the same as R' or corresponds to the formula $R^3(OCH_2CH_2)_nS-$, wherein $R^3$ is as defined above. Although it is desirable that $R^4$ is the same as R' and X' is sulfur, a preferred embodiment is a mixture of isomers with alkyl dithiophosphoric acid as described in U.S. Pat. No. 3,909,447.

The corrosion inhibiting activity of the above-described compounds are especially useful in liquid hydrocarbons and petrochemicals during the processing thereof where the process temperature is elevated to about 175° C. to about 400° C. or higher (e.g., 540° C.). The additives are especially useful at process temperatures of about 205° C. to about 400° C. or higher and in particular where the liquid is acidic and more particularly where the acidity is due at least in part by the presence therein of corrosion inducing amounts of naphthenic acid or other similar organic acids or phenols such as cresylic acid. This method is particularly suited to nonaqueous liquids and to protection of iron-containing metal surfaces.

The most effective amount of the corrosion inhibitor or mixture of inhibitors to be used in accordance with this invention can vary, depending on the local operating conditions and the particular hydrocarbon being processed. Thus, the temperature and other characteristics of the acid corrosion system can have a bearing on the amount of the inhibitor or mixture of inhibitors to be used.

Generally, where the operating temperatures and/or the acid concentrations are higher, a proportionately higher amount of the corrosion inhibitor will be required. It has been found that the concentration of the corrosion inhibitor or mixture of inhibitors may range from about 10 ppm to about 5,000 ppm or higher. It has also been found that it is preferred to add the inhibitors at a relatively high initial dosage rate of about 2,000 ppm to about 5,000 ppm and to maintain this level for a relatively short period of time until the presence of the inhibitor induces the build-up of a corrosion protective coating on the metal surfaces. Once the protective surface is established, the dosage rate needed to maintain the protection may be reduced to a normal operational range of about 10–25 ppm without substantial sacrifice of protection.

While the gas oil and light lubricating oil fractions often contain naphthenic acid which contributes to the corrosion problem which the present invention especially relieves, the anticorrosion additives are not only useful in inhibiting corrosion in a part of a refinery handling these petroleum intermediates but are useful throughout an oil refinery where acidic hydrocarbons are in contact with iron-containing metal surfaces.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples, all percentages are given on a weight basis unless otherwise indicated.

EXAMPLE 1.

Alkyl dithiophosphoric acid derivative was prepared by ethoxylating Alfol 8-10, and then reacting the ethoxylated Alfol 8-10 with $P_2S_5$. "Alfol" is a trade designation of Vista Chemical for a mixture of primary straight chain alcohols made by Ziegler-type reaction of aluminum alkyls, ethylene and hydrogen; in the case of Alfol 8-10, the alcohols are $C_8$ to $C_{10}$ alcohols. The resulting composition comprised predominantly the alkyl dithiophosphoric acid derivative of the formula

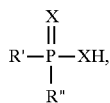

wherein R' and R" are each $R^3(OCH_2CH_2)_n$—O—, each X is sulfur, the $R^3$'s are alkyl groups of eight to ten carbons and n is from three to five. The composition also comprised a lesser amount of dimer of the alkyl dithiophosphoric acid, formed as a side product.

EXAMPLE 2.

In this example, various amounts of a 50% formulation of the composition prepared in accordance with Example 1, above, were tested for corrosion inhibitive efficacy on steel coupons in a hot gas oil containing naphthenic acid and compared in such efficacy to thiazoline-based chemistry and $C_{8-10}$ phosphate esters.

The total acid number (TAN) of the gas oil was measured as 4.2. Although a temperature of about 600° F. (about 320° C.) was desired for the tests, the gas oil contained a considerable amount of light ends, making 570° F. (about 300° C.) the upper temperature limit for the gas oil and even then refluxes posed problems. Therefore, although the temperature of the gas oil in the earlier tests was maintained at about 570° F. (about 300° C.), in some of the later tests, the gas oil was maintained at about 525° F. (about 275° C.).

The duration of most of the tests was about six to seven hours, which is a relatively short period considering that corrosion rate is generally highest at the beginning and then tapers off. Thus, the corrosion rates for these tests appear higher than would the rates derived from tests of longer duration. A few of the tests were run for longer periods, particularly twenty and 31.25 hours. For these longer runs, the coupons were held in a kettle of the test mixture for a little over six hours a day, after which time each day the coupons were removed and rinsed.

The results of the tests are in the table below, in which the additives are identified as "Example 1" for the 50% formulation of the composition prepared in Example 1, above, "Thiazoline" for the thiazoline-based derivative, and "Phos Ester" for the $C_{8-10}$ phosphate ester, the additive concentration ("Dose") is given in ppm by weight, the average weight loss ("Ave Wgt Loss") for the three coupons in each test is given in milligrams, the temperature ("Temp") of the gas oil in each test is given in the format x/y wherein x is the temperature in °F. and y is the temperature in °C., the duration of the test is given in hours and the corrosion rate ("Corr Rate") measured in each test is given in mils per year.

| Additive | Dose | Temp | Duration | Ave Wgt Loss | Corr Rate |
|---|---|---|---|---|---|
| None | — | 570/300 | 6.5 | 16 | 120 |
| None | — | 570/300 | 6.5 | 17.5 | 137 |
| None | — | 570/300 | 20 | 22.9 | 56 |
| None | — | 575/302 | 20 | 22.5 | 55 |
| Thiazo-line | 2500 | 570/300 | 5.5 | 10 | 88 |
| Thiazo-line | 5000 | 570/300 | 6.5 | 4.07 | 30.5 |
| Thiazo-line | 5000 | 552/289 | 6.25 | 3.5 | 27.3 |
| Thiazo-line | 5000* | 525/274 | 31.25 | 6.2 | 9.7 |
| Phos Ester | 2500 | 581/305 | 6.25 | 9.4 | 73.3 |
| Example 1 | 2500 | 525/274 | 6.75 | 1.7 | 12.3 |
| Example 1 | 5000 | 570/300 | 6.25 | 2.37 | 18.7 |
| Example 1 | 5000 | 525/274 | 6.25 | 3.2 | 24.9 |
| Example 1 | 5000* | 525/274 | 31.25 | 2.5 | 3.9 |

*The starting dosage was 5,000 ppm, applied on the first day. The dosage was then cut in half on each of four successive days, with the final dosage level being about 300 ppm.

EXAMPLE 3

Further tests were carried out in accordance with the procedure of Example 2, above. In these tests, the additive of Example 1 was compared with a thiophosphinic acid derivative and an unethoxylated alkyl dithiophosphoric acid, both of which are also within the scope of the subject invention. The thiophosphinic acid derivative corresponded to the formula $(R^3(OCH_2CH_2)_{3-5})_2P(:S)SH$, wherein $R^3$ is a $C_{8-10}$ alkyl group derived from Alfol 8-10. The alkyl dithiophosphoric acid corresponded to the formula $(R^3O)_2P(:S)SH$, wherein $R^3$ is a $C_{8-10}$ alkyl group derived from Alfol 8-10; that is, it was similar to the additive of Example 1, but was not ethoxylated. The tests were carried out with carbon steel coupons in heavy vacuum gas oil at 600° F. (316° C.) for twenty hours. The total acid number (TAN) of each test was about 5 mg KOH/gm oil. The dosage of the additive in each case (other than the blanks) was 1 ml of additive (50% active) per liter gas oil. The results were as follows, wherein the corrosion rate ("Corrosion Rate") measured in each test is given in mils per year and is the average for the three coupons in the test:

| Additive | Corrosion Rate |
|---|---|
| None | 32.4 |
| None | 33.4 |
| Alkyl Dithiophosphoric Acid | 3.3 |
| Alkyl Dithiophosphoric Acid | 3+ |
| Thiophosphinic Acid Derivative | 4.97 |
| Thiophosphinic Acid Derivative | 5.27 |
| Example 1 | 2.60 |
| Exmnple 1 | 2.6+ |

In view of the above, it will be seen that the several advantages of the invention are achieved and other advantageous results obtained.

As various changes could be made in the above methods and composition without departing from the scope of the invention, it is intended that all matter contained in the above description shall be interpreted as illustrative and not in a limiting sense.

What is claimed is:

1. A method for inhibiting naphthenic acid corrosion of iron-containing metal surfaces in a non-aqueous hydrocarbon fluid having a temperature of from about 175° C. to about 400° C. and containing a corrosive amount of naphthenic acid, comprising adding to said fluid or to a feed therefor, in a total additive amount sufficient to effect corrosion inhibition in said fluid, at least one of the following types of compounds:

a. thiophosphorus compounds of the formula

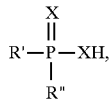

wherein R' is selected from the group consisting of $R^3(OCH_2CH_2)_n$- and $R^3(OCH_2CH_2)_nO$—, R" is selected from the group consisting of $R^3(OCH_2CH_2)_n$- and $R^3(OCH_2CH_2)_nO$—, and —XH, wherein each X is independently selected from the group consisting of sulfur and oxygen, provided however that at least one X is sulfur, $R^3$ is an alkyl group of about 6 to about 18 carbon atoms and n is an integer from 1 to about 12, b. salts of said thiophosphorus compounds,
c. alkyl and aryl esters of said thiophosphorus compounds, and
d. isomers of said thiophosphorus compounds, thereby to effect inhibition of naphthenic acid induced corrosion in said fluid.

2. A method as set forth in claim 1 wherein each X is sulfur.

3. A method as set forth in claim 2 wherein R' and R" are the same or different and each corresponds to the formula $R^3(OCH_2CH_2)_nO$—.

4. A method as set forth in claim 3 wherein R' is the same as R".

5. A method as set forth in claim 3 wherein n is 0.

6. A method as set forth in claim 3 wherein n is an integer from about three to about five.

7. A method as set forth in claim 3 wherein $R^3$ is an alkyl group of from about eight to about ten carbons.

8. A method as set forth in claim 6 wherein $R^3$ is an alkyl group of from about eight to about ten carbons.

9. A method as set forth in claim 1 wherein the alkyl and aryl esters of said thiophosphorus compounds contain up to about eighteen more carbon atoms than do the corresponding thiophosphorus compounds themselves.

10. A method as set forth in claim 9 wherein the alkyl and aryl esters of said thiophosphorus compounds contain up to about twelve more carbon atoms than do the corresponding thiophosphorus compounds themselves.

11. A method as set forth in claim 1 wherein the hydrocarbon fluid is crude oil undergoing refining and cracking.

12. A method as set forth in claim 3 wherein each X in the formula for the thiophosphorus compound represents sulfur and the isomers correspond to the formula

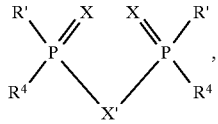

wherein X represents sulfur, X' represents sulfur or oxygen, R' is as defined for the formula for the thiophosphorus compound and $R^4$ is the same as R' or corresponds to the formula $R^3(OCH_2CH_2)_nS$—, wherein $R^3$ is as defined in claim 1.

13. A method as set forth in claim 12 wherein each n is 0.

14. A method as set forth in claim 12 wherein each n is an integer from about 3 to about 5.

15. A method as set forth in claim 12 wherein $R^3$ is an alkyl group of about 6 to about 18 carbon atoms.

16. A method as set forth in claim 14 wherein $R^3$ is an alkyl group of about 6 to about 18 carbon atoms.

17. A method as set forth in claim 12 wherein the alkyl and aryl esters of said thiophosphorus compounds contain up to about eighteen more carbon atoms than do the corresponding thiophosphorus compounds themselves.

18. A method as set forth in claim 16 wherein the alkyl and aryl esters of said thiophosphorus compounds contain up to about eighteen more carbon atoms than do the corresponding thiophosphorus compounds themselves.

19. A method as set forth in claim 12 wherein the hydrocarbon fluid is crude oil undergoing refining and cracking.

20. A method as set forth in claim 3 wherein at least one of the thiophosphorus compounds, or the salts or the alkyl or aryl esters thereof, and at least one of the isomers are added to the fluid or the feed therefor.

21. A method as set forth in claim 20 wherein at least two of the isomers are added to the fluid or the feed therefor.

22. A method as set forth in claim 21 wherein the isomers correspond to the formula

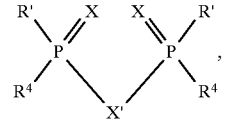

wherein X represents sulfur, X' represents sulfur or oxygen, R' is as defined for the formula for the thiophosphorus compound and $R^4$ is the same as R' or corresponds to the formula $R^3(OCH_2CH_2)_nS$—, wherein $R^3$ is as defined in claim 1.

23. A method as set forth in claim 22 wherein the one of the isomers corresponds to the formula

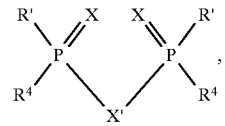

wherein X and X' each represents sulfur, R' is as defined for the formula for the thiophosphorus compound, $R^4$ is the same as R' and $R^3$ is as defined in claim 1, and another isomer corresponds to the formula

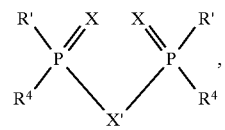

wherein X represents sulfur, X' represents oxygen, R' is as defined for the formula for the thiophosphorus compound, $R^4$ corresponds to the formula $R^3(OCH_2CH_2)_nS$— and $R^3$ is as defined in claim 1.

24. A method as set forth in claim 1 wherein R' and R" each correspond to $R^3(OCH_2CH_2)_n$-.

25. A method as set forth in claim 24 wherein each X is sulfur.

26. A method as set forth in claim 24 wherein the X double-bonded to the phosphorus is sulfur.

27. A method as set forth in claim 1 wherein R" corresponds to —XH.

28. A method as set forth in claim 27 wherein each X is sulfur.

29. A method as set forth in claim 27 wherein the X double-bonded to the phosphorus is sulfur.

30. A method as set forth in claim 1 wherein the hydrocarbon fluid is gas oil.

31. A method as set forth in claim 1 wherein the hydrocarbon fluid is a liquid.

32. A method as set forth in claim 2 wherein the hydrocarbon fluid is a liquid.

33. A method as set forth in claim 3 wherein the hydrocarbon fluid is a liquid.

34. A method as set forth in claim 8 wherein the hydrocarbon fluid is a liquid.

35. A method as set forth in claim 10 wherein the hydrocarbon fluid is a liquid.

36. A method as set forth in claim 12 wherein the hydrocarbon fluid is a liquid.

37. A method as set forth in claim 1 wherein the temperature of the hydrocarbon fluid is at least about 205° C.

* * * * *

UNITED STATES PATENT AND TRADEMARK OFFICE
CERTIFICATE OF CORRECTION

PATENT NO. : 5,863,415
DATED : January 26, 1999
INVENTOR(S) : Zetlmeisl

It is certified that error appears in the above-identified patent and that said Letters Patent is hereby corrected as shown below:

In claim 1, at line 24, the clause that begins with the word "thereby" should be moved so that it starts a new line that begins at the left margin of line 25. The claim should appear as follows:

1. A method for inhibiting naphthenic acid corrosion of iron-containing metal surfaces in a non-aqueous hydrocarbon fluid having a temperature of from about 175°C. to about 400°C. and containing a corrosive amount of naphthenic acid, comprising adding to said fluid or to a feed therefor, in a total additive amount sufficient to effect corrosion inhibition in said fluid, at least one of the following types of compounds:
   a. thiophosphorus compounds of the formula

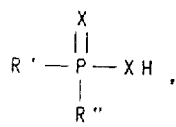

UNITED STATES PATENT AND TRADEMARK OFFICE
CERTIFICATE OF CORRECTION

PATENT NO. : 5,863,415
DATED : January 26, 1999
INVENTOR(S) : Zetlmeisl

It is certified that error appears in the above-identified patent and that said Letters Patent is hereby corrected as shown below:

wherein R' is selected from the group consisting of $R^3(OCH_2CH_2)_n$- and $R^3(OCH_2CH_2)_nO$-, R" is selected from the group consisting of $R^3(OCH_2CH_2)_n$- and $R^3(OCH_2CH_2)_nO$-, and -XH, wherein each X is independently selected from the group consisting of sulfur and oxygen, provided however that at least one X is sulfur, $R^3$ is an alkyl group of about 6 to 18 carbon atoms and n is an integer from 1 to about 12,
      b.     salts of said thiophosphorus compounds,
      c.     alkyl and aryl esters of said thiophosphorus compounds, and
      d.     isomers of said thiophosphorus compounds,
thereby to effect inhibition of naphthenic acid induced corrosion in said fluid.

Signed and Sealed this

Eighth Day of June, 1999

*Attest:*

Q. TODD DICKINSON

*Attesting Officer*     *Acting Commissioner of Patents and Trademarks*